United States Patent [19]

Luper

[11] Patent Number: 4,509,551
[45] Date of Patent: Apr. 9, 1985

[54] BREATH SWITCH

[75] Inventor: Charles R. Luper, Anaheim, Calif.

[73] Assignee: Sensormedics Corporation, Anaheim, Calif.

[21] Appl. No.: 453,414

[22] Filed: Dec. 27, 1982

[51] Int. Cl.³ ............................................. F16K 37/00
[52] U.S. Cl. .................................. 137/554; 137/512.3; 137/855; 128/725; 128/204.23; 116/270
[58] Field of Search ........... 128/724, 725, 727, 204.21, 128/204.23; 340/606, 608, 610, 611; 116/112, 270; 222/639, 644; 73/202, 203; 137/512 B, 552.7, 554, 855; 250/229; 200/81.9 R

[56] References Cited

U.S. PATENT DOCUMENTS

| | | | |
|---|---|---|---|
| 2,773,251 | 12/1956 | Snyder | 200/81.9 R |
| 2,972,345 | 2/1961 | Spigel | 128/204.23 |
| 3,357,428 | 12/1967 | Carlson | 128/204.23 |
| 3,455,314 | 7/1969 | Glick et al. | 137/552.7 X |
| 4,190,045 | 2/1980 | Bartels | 128/205.24 |
| 4,297,899 | 11/1981 | Blaney et al. | 73/861.58 |
| 4,443,671 | 4/1984 | Hinds | 340/606 X |
| 4,456,016 | 6/1984 | Nowacki et al. | 128/725 |

Primary Examiner—James L. Rowland
Assistant Examiner—Brian R. Tumm
Attorney, Agent, or Firm—Lyon & Lyon

[57] ABSTRACT

An improved switching device for indicating the beginning and ending of the breath of a test subject. A flow through housing is provided with an inlet and first and second outlets. A flexible diaphragm is connected in series with the first outlet to serve as a check valve which opens during the high flow rate portion of a breath. A sensitive flow responsive member connected in series with the second outlet opens in response to the presence of gas flow during the low flow rate portion of the breath. A detecting circuit responsive to the position of the flow responsive member accurately signals the beginning and ending of a breath. A damping member connected to the flexible diaphragm prevents the latter from vibrating at low breath flow rates and thereby stabilizes the motion of the flow responsive member.

8 Claims, 10 Drawing Figures

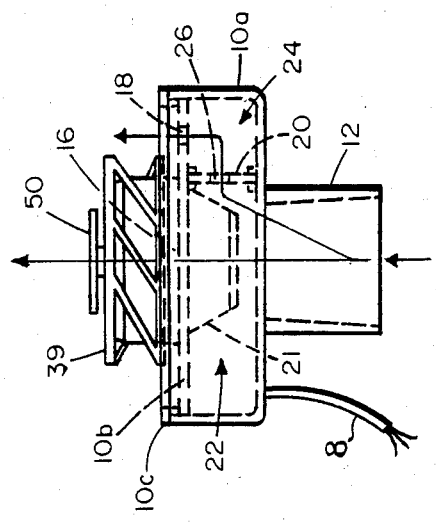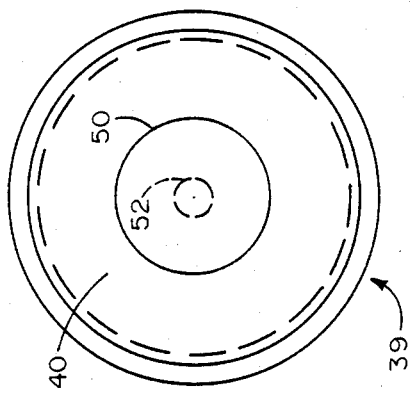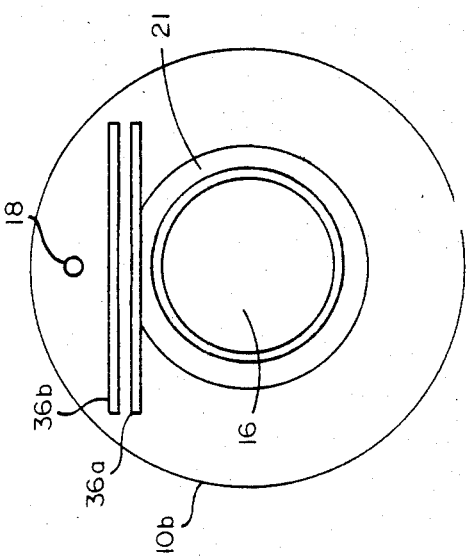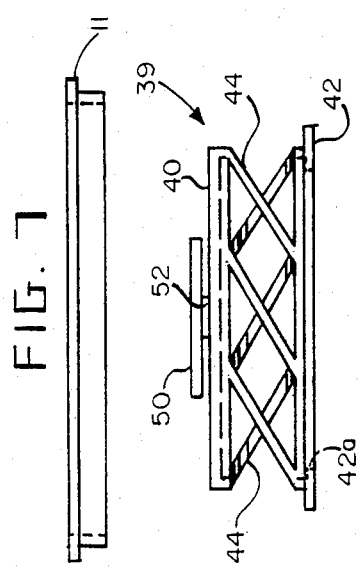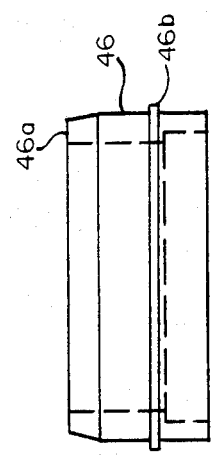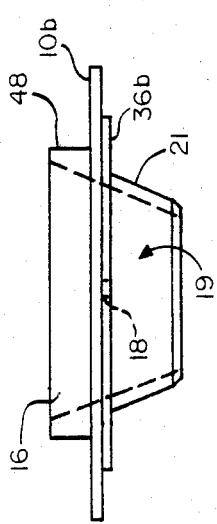

4,509,551

BREATH SWITCH

BACKGROUND OF THE INVENTION

The present invention relates to flow responsive switches and is directed more particularly to a flow responsive switch for indicating the beginning and ending of the breath of a test subject.

In evaluating the physical condition of a test subject, useful information can be derived by measuring the volume and composition of the test subject's exhaled breath. Instruments for performing these measurements usually include gas analyzers for measuring at least the concentration of oxygen and carbon dioxide in the exhaled breath. Measurements of this type may be performed under conditions which range from a condition of rest to a condition of vigorous exercise. In order to properly interpret the measurements, however, it is necessary to take into account the volume of the breath. This volume, in turn, is usually measured indirectly by measuring the rate of flow and duration of each breath.

The rate of flow of a breath is conveniently measured by directing the breath through a gas turbine which is arranged to generate a series of pulses having a repetition rate that varies with the rate of gas flow therethrough. Because of the non-linearity of gas turbines, the volume of a breath can be determined from the number of pulses it produces only by taking into account the duration of a breath. The number of pulses and' the duration of that breath may, for example, be combined to produce a pulses-per-second value which can then be combined with the known characteristics of the turbine to yield the volume of that breath.

In making the above measurement it has been found that much of the error that occurs results not from the operation of the turbine, but rather from the inaccurate determination of the duration of the breath. An accurate determination of the end of a breath has been found to be particularly difficult because of the low rates of flow that are associated therewith when the test subject is at rest.

Prior to the present invention, it was the practice to direct a flow of bias gas through the turbine and thereby cause the latter to generate a predetermined minimum number of turbine pulses per unit time. With the use of this approach the beginning of breath is taken as the time when the pulse "frequency" increases above its minimum value, and the ending of the breath is taken as the time when the pulse "frequency" returns to that minimum value. Because the beginning of a breath is usually characterized by a relatively sudden increase in the rate of gas flow, the time at which a breath begins can be determined relatively accurately in this way. Because, however, the ending of a breath is characterized by a low and slowly changing rate of flow, the time at which a breath ends cannot be determined accurately in this way. As a result, the measured duration of a breath can be in error by several percent, causing a corresponding error in the measured volume of the breath.

SUMMARY OF INVENTION

In accordance with the present invention there is provided an improved breath duration measuring device, hereinafter referred to as a breath switch, which signals the beginning and ending of breath with improved accuracy and which does not require the use of a bias gas flow. Generally speaking, the breath switch of the invention includes a housing that provides first and second paths through which a breath may be vented to the atmosphere. The first or main flow path conducts the flow of most of an exhaled breath through a check valve comprising a flexible diaphragm which is gently biased in its closed position. Because of this biasing, the valve will open only when the pressure of an exhaled breath exceeds a predetermined minimum value. Once open, however, the check valve provides little fluidic resistance to the flow of a breath.

The second flow path through the housing bypasses the check valve and thereby allows an exhaled breath to continue to flow after the check valve closes. This second flow path is provided with a flow responsive member which is highly sensitive to the flow breath. The position of this member is used to signal the beginning and ending of a breath and thereby provide duration data of greatly improved accuracy.

In the preferred embodiment, the flow responsive member is a flexible metal foil which is connected across the second flow path and which is arranged to interrupt or not interrupt a beam of light which is established by an associated optoelectronic detector circuit. Because of the flexibility of the flow responsive member it is able to clearly signal the beginning and ending of breath, even at the extremely low flow rates that may be associated with those conditions. The detector circuit is therefore able to provide a sensitive and unambiguous indication of the duration of a breath.

In order to stabilize the motion of the flow responsive member at very low breath flow rates, a flexible damping member is connected to the flexible diaphragm. This damping member preferably vibrates at a frequency which destructively interferes with the vibrations of the flexible diaphragm, and thereby stabilizes the opening and closing of the check valve. The stabilization of the check valve, in turn, eliminates the tendency of the flow responsive member to vibrate or "flutter" at very low breath flow rates. As a result, the flow responsive member is able to accurately signal the beginning and ending of a breath over the entire range of breath flow rates.

Together, the above features allow the breath switch of the invention to have the sensitivity necessary to accurately measure the beginning and ending of breath at low flow rates, and yet be able to deal with the high breath flow rates that are associated with the taking of measurements under exercise conditions.

DESCRIPTION OF THE DRAWINGS

FIG. 4a shows a bottom view of the element shown in FIG. 4, FIG. 6a shows a top view of the element shown in FIG. 6, FIG. 7 shows a side view of a retaining ring that holds the upper and lower parts of the housing together, and FIG. 8 shows the appearance of the fully assembled breath switch.

DESCRIPTION OF THE PREFERRED EMBODIMENTS

Figure 1:
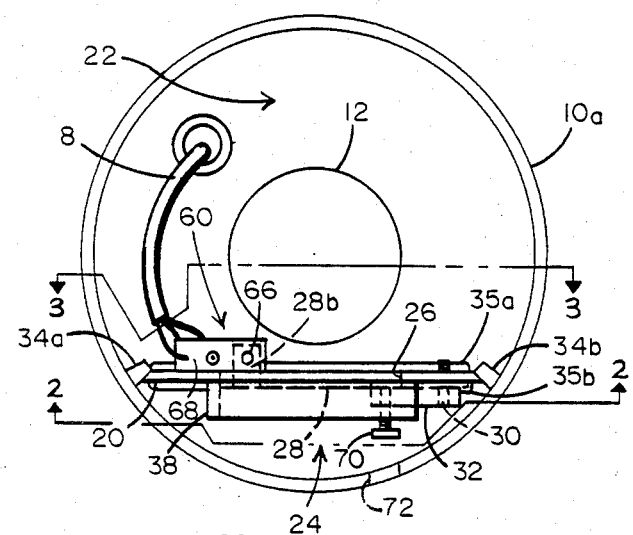
FIG. 1 is a top view of the breath switch of the invention, shown with the upper part of its housing removed.
Figure 2:
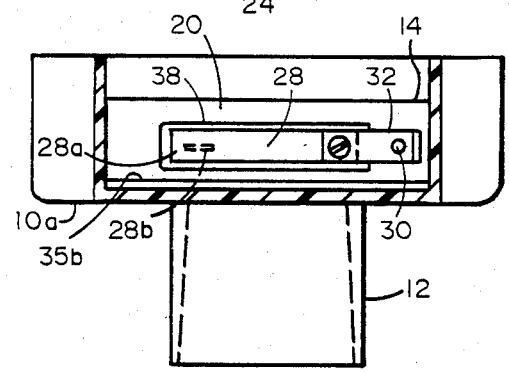
FIG. 2 is a cross-sectional view of the switch of FIG. 1 taken along the section line 2—2.
Figure 3:
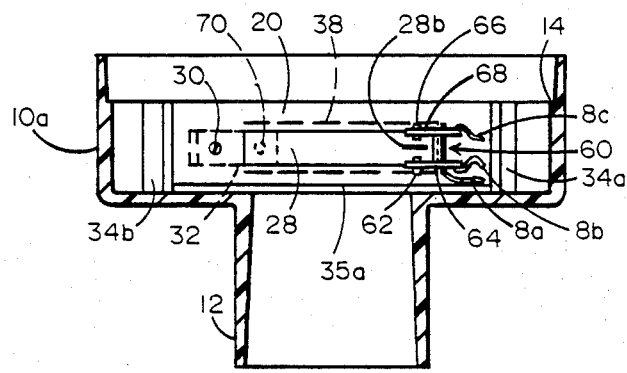
Figure 3 is a cross-sectional view of the switch of FIG. 1 taken along the section line 3—3, FIGS. 4, 5, 6 and 7 together comprise an exploded view of the upper part of the housing of the breath switch of the invention.

FIGS. 1, 2 and 3 include a top and two crosssectional views of the lower half of the breath switch of the invention. This lower half fits together with an upper half, which is shown in exploded form in FIGS. 4, 5, 6 and 7 to form a complete breath switch assembly. The complete assembly, the appearance of which is shown in FIG. 8, is adapted to be connected in series with the outlet of a breath gas analyzer (not shown) and to apply to the conductors of a cable 8 electrical signals which indicate beginning and ending of breath flow.

As shown in FIGS. 1, 2 and 3, the lower half of the breath switch includes a first housing section 10a. This housing section, which is preferably made of a suitable injection molded plastic, includes a gas inlet 12 which is adapted to be connected in series with the outlet of the breath gas analyzer. Inlet 12 preferably includes a tapered interior surface 11 which can fit over and be supported by the outlet of a gas turbine (not shown) which measures the rate of gas flow through the analyzer.

Housing section 10a is provided with an internal mounting shoulder 14 which is clearly visible in FIG. 3. This shoulder serves as a stop for a second housing section 10b, shown in FIGS. 4 and 8, which fits into housing section 10a to form a closed housing. Housing section 10b is held in place with respect to housing section 10a by a suitable retaining ring 11, shown in FIG. 7, which may be attached to housing section 10a by suitable screws (not shown). By closing the upper end of housing section 10a, housing section 10b forces the gas that flows into inlet 12 to flow out of one or the other or both of two outlets. The first outlet, 16, shown in FIGS. 4 and 4a, is relatively large and occupies the central part of housing section 10b. This outlet serves to conduct the greater part of the flow of an exhaled breath. The second outlet, 18, has a relatively small area and is located to one side of first outlet 16. Outlet 18 serves to conduct the lesser part of the flow of an exhaled breath, except under those conditions in which first outlet 16 is blocked, as will be explained more fully hereafter. These first and second outlets are associated with two different respective flow paths through the interior of the breath switch.

Referring again to FIG. 1, there is shown a partition or wall 20 which serves to divide the interior of the housing into a first chamber 22 and a second chamber 24. First chamber 22, which is connected between inlet 12 and first outlet 16, provides a first path for the flow of breath through the housing. Second chamber 24, which is connected between inlet 12 and second outlet 18, through chamber 22, provides a second flow path for the flow of gas through the housing. During operation, breath will flow through the second or through the first and second of these paths, depending upon the rate of flow or force of that breath.

Partition 20 is provided with an elongated opening or slot 26 in which is located a flexible flow responsive member or flapper 28 that is attached to partition 20 by a suitable mounting screw 30 that is best seen in FIGS. 1 and 3. This screw preferably passes through member 28 and screws into a threaded hole in a mounting block 32 to hold member 28 against partition 20.

When no gas flows through the breath switch, member 28 assumes a rest or unactuated position as shown in FIGS. 1 through 3. In this position member 28 substantially blocks opening 26, except for clearance spaces, that are too small to be clearly shown, which lie along the edges of member 28. When, on the other hand, gas does flow through the breath switch, member 28 is displaced from the position shown in FIG. 1 to assume its actuated position. In the latter position member 28 is flexed or bent so that the tip 28a thereof moves out of opening 26 and provides a clear path for the flow of gas between chambers 22 and 24. Thus, flow responsive member 28 assumes one of two positions or states depending upon the presence or absence of breath flow at inlet 12.

In order to make member 28 sensitive to very low rates of breath flow, member 28 is preferably made of a material, such as a metal foil, which is sufficiently flexible to bend readily when a pressure difference appears across it, but which is sufficiently resilient to return to its original position when the pressure difference is removed. One material which has been found to have these properties is a one mil piece of austenitic stainless steel. Other suitable materials will be apparent to those skilled in the art.

In the preferred embodiment, partition 20 is provided with a projecting channel 38 that surrounds at least the movable portion of member 28. The effect of projecting channel section 38 is to reduce the amount of gas that flows past the upper and lower edges of member 28 and thereby cause the gas in the second flow path to concentrate at the end 28a thereof. Since the end of member 28 is the most easily moved part thereof, this assures that even a small difference between the pressures in chambers 22 and 24 produces a relatively large movement of end 28a of member 28.

The sensitivity of the flow responsive member may be further enhanced by including in housing section 10b an elongated tapered passage 19 between chamber 22 and outlet 16. Because the wall of this passage defines a tapered surface 21 which projects downwardly to a point above inlet 12, as shown in FIG. 8, it tends to deflect a part of the entering gas stream toward the periphery of housing section 10a. This outward deflection of the entering gas stream has in some cases been found to improve the dynamic response of member 28 by concentrating the flow of gas thereagainst. Accordingly, a flow deflecting surface such as 21 which is located adjacent to slot 26 is regarded as a desirable but not essential feature of the present invention.

During the taking of measurements, it is important that gas not be drawn into the gas analyzer, through outlet 16, when the test subject is inhaling. This is because such an inward flow of gas would mix atmospheric gas with the previously exhaled breath gases that are still in the analyzer and thereby introduce an error into the gas concentration readings. In order to prevent this from occurring, the breath switch is provided with a check valve 39 which fits over outlet 16 in housing section 10b. In the preferred embodiment check valve 39 includes a flexible elastomeric diaphragm 40 which is shown in FIGS. 6 and 6a. As shown in FIG. 6, diaphragm 40 is connected to a circular base 42 by strips 44 which are formed integrally with diaphragm 40 and base 42. These connecting strips serve as springs to pull diaphragm 40 downwardly, toward base 42, to close the check valve when no offsetting force tends to move diaphragm 40 in the opposite direction.

During assembly, check valve 39 is pulled down over an annular member 46, shown in FIG. 5, until the inwardly projecting lip 42a of base 42 slips over and locks into place around an outwardly projecting ridge 46b on member 46. Member 46 is then pushed down over the raised rim 48 of outlet 16 where it is held by the tightness of the fit and effectively becomes a part of housing section 10b. When check valve 39 is properly positioned with respect to membrane 46, diaphragm 40 will rest on the upper edge 46a of member 46 which acts as a valve seat, will be pushed against that valve seat with the desired force. This force is such that diaphragm 40 will lift off of valve seat 46a to open the check valve when the pressure of an exhaled breath exceeds a threshold value that is low enough to prevent the application of objectionable back pressure to the test subject. Diaphragm 40 will therefore tend to remain closed at the beginning and ending of each breath, but will open to provide a low resistance path for breath flow during the high flow rate portion thereof.

Because of the elasticity of diaphragm 40, it tends to vibrate or flutter at low breath flow rates. This flutter is undesirable because it can cause unintended fluctuations in the position of flow responsive member 28. In order to eliminate these fluctuations, a flexible elastomeric vibration damping member 50 is attached to the upper surface of diaphragm 40 by a drop 52 of a suitable glue. Because it is sized differently than diaphragm 40, damping member 50 tends to vibrate at a different frequency. In the preferred embodiment damping member 52 is so sized relative to diaphram 40 that its vibrations destructively interfere with those of diaphragm 40 and thereby stabilize the operation of valve 39. This stabilization has been found to significantly improve the ability of the breath switch to precisely detect the beginning and ending of a breath.

In accordance with the present invention, the flexibility of member 28 is such that it will assume its actuated position when the pressure in chamber 22 is too low to open check valve 39. This same flexibility permits member 28 to remain in its actuated position after the pressure in chamber 22 becomes too low to hold check valve 39 open. Since, such low pressure conditions exist at the beginning and ending of a breath, changes in the position of member 28 signal the beginning and ending of a breath with much greater sensitivity than changes in the position of check valve 39.

During the high pressure, high flow rate portion of a breath, check valve 39 will open to provide a low resistance to the flow of breath through the first flow path and opening 16. This low resistance path effectively bypasses the flow of breath through the second flow path and outlet 18, and thereby prevents the application of objectionable back pressure to the test subject. Since, however, the pressure that is necessary to hold the check valve open is high enough to keep member 28 from returning to its rest position, member 28 will remain in its actuated position during the high flow rate portion of an exhaled breath. Thus, member 28 will remain in its actuated position during both the high and low flow rate portions of a breath.

To the end that the position of flow responsive member 28 may be communicated to the instrument with which the breath switch is used, the breath switch is provided with a detecting circuit 60 which is shown in FIGS. 1 and 3. In the preferred embodiment detecting circuit 60 is an optoelectronic circuit including a light emitting device such as an LED 62 which is mounted on a first circuit board 64, and a light responsive device such as a phototransistor 66 which is mounted on a second circuit board 68. LED 62 is supplied with operating power through conductors 8a and b of cable 8. Similarly, phototransistor 66 is supplied with operating power through conductors 8a and c of cable 8. The connections between the conductors 8a through c and devices 62 and 66 are made via conductive traces which are deposited on the two sides of circuit boards 64 and 68 in a manner well known to those skilled in the art.

In order that the transmission of light from LED 62 to phototransistor 66 may be controlled in accordance with the position of member 28, member 28 is provided with a light interrupting vane 28b which projects through slot 26. When member 28 is in its rest position, vane 28b blocks the transmission of light from LED 62 to phototransistor 66. Under this condition, only a small current will flow in conductors 8a and c. When even a gentle flow of breath is present, however, member 28 will assume its actuated position to remove vane 28b from between LED 62 and phototransistor 66 and thereby permit light to be transmitted therebetween. Under this condition, a sizable current will flow in conductors 8a and c. It will therefore be seen that the current in conductors 8a and c is direct and sensitive indication of the beginning and ending, and therefore the duration of a breath. It will be understood that other detecting circuits, such as those using hall effect devices, may be substituted for the optoelectronic circuitry shown in FIG. 3 without significantly affecting the operation thereof.

During the time that a test subject is breathing in, the low pressure in chamber 22 tends to draw member 28 inwardly through slot 26. Because this movement can cause small amounts of air to be drawn in inwardly through outlet 18, it is desirable to keep such movement to a minimum. One convenient way of limiting this inward movement is to position circuit boards 64 and 68 so that the edges thereof act as stops for member 28. By limiting the movement of member 28 these stops cause member 28 to act as a check valve to block the flow of air from outlet 18 into chamber 22. Other ways of blocking the inward flow of air through outlet 18 will be apparent to those skilled in the art.

To the end that member 28 may be adjusted so that it assumes the rest position shown in FIG. 1, there is provided an adjustment screw 70. This screw, which passes through a threaded hole in mounting block 32, pushes against member 28 near the non-movable end thereof. By turning screw 70 in one direction or the other the rest position of member 28 may be moved further into or out of slot 26. Since adjustment screw 70 can push but not pull member 28, it is desirable that any natural curvature in member 28 be such that the latter pushes against screw 70. External access to adjusting screw 70 is conveniently provided via an access hole 72 through housing section 10a. Because this access hole is fluidically in parallel with outlet 18, it does not interfere with the operation of blocking member 28.

In order to make the breath switch easy to produce and assemble, partition 20 is preferably formed as a separate piece and not as a part of housing sections 10a or 10b. This separateness makes it possible to attach to partition 20 all of the mechanical and electrical devices that are mounted thereon before partition 20 is inserted into the housing. This separateness also makes it necessary, however, to provide retaining structures which can receive and hold the edges of partition 20 and thereby assure that partition 20 is held in the proper position within the housing. In housing section 10a the retaining structures include vertical retaining strips 34a and 34b and horizontal retaining strips 35a and 35b, all of which project inwardly from the inner surface of housing section 10a. In housing section 10b the retaining structures include retaining strips 36a and 36b which project inwardly from the inner surface of that housing section. By slipping into the spaces between these retaining strips, partition 20 is held firmly in the desired position within the housing. In the latter position, partition 20 substantially prevents gas from flowing into chamber 24 around the edges thereof.

While chamber 24 is shown as being connected to inlet 12 through chamber 22, chamber 24 may also be directly connected to inlet 12. Inlet 12 may, for example, be partitioned into a first large inlet section which leads directly to chamber 22 and a second, smaller inlet section which leads directly to chamber 24. Because, however, embodiments of the latter type provide no advantage over the embodiment of FIGS. 1 through 6, and complicate the internal structure of the housing, they are not regarded as preferred embodiments of the present invention. They are nevertheless considered to be within the scope of the present invention.

In view of the foregoing it will be seen that a breath switch constructed in accordance with the present invention provides a number of advantages over previously used breath duration measuring devices. In particular the breath switch of the invention can detect the beginning and ending of a breath with greater accuracy and sensitivity than previously used devices. In addition the breath switch of the invention makes possible the elimination of the cost that is associated with the use of a bias gas source. Finally, the breath switch of the invention includes an improved vibration damped check valve which eliminates the potential gas flow instabilities that are associated with low gas flow rates.

What is claimed is:

1. A switch for indicating the beginning and ending of a pulsatile flow of gas comprising:
    (a) a housing having an inlet and first and second outlets,
    (b) means defining a first flow path for the flow of gas between the inlet and the first outlet,
    (c) means defining a second flow path for the flow of gas between the inlet and the second outlet,
    (d) a check valve including a flexible diaphragm connected in series with the first flow path,
    (e) a flow responsive member connected in series with the second flow path and adapted to move in response to the flow of gas through the second flow path,
    (f) means for indicating the position of said flow responsive member, and
    (g) a vibration damping member attached to said flexible diaphragm.

2. The switch of claim 1 in which the flexible diaphragm comprises a first elastomeric disc having a first diameter, and in which the vibration damping member comprises a second elastomeric disc having a diameter smaller than said first diameter.

3. The switch of claim 2 in which the center of said second disc is attached to the center of said first disc.

4. A switch for measuring the duration of a pulsatile flow of gas comprising:
    (a) a housing having an inlet and first and second outlets,
    (b) a first housing chamber open to the inlet and the first outlet,
    (c) a second housing chamber open to the second outlet,
    (d) a check valve including a flexible diaphragm connected in a series with the first outlet,
    (e) means defining a passage between the first and second chambers,
    (f) a flow responsive member located in said passage, said flow responsive member being adapted to assume a rest position when approximately no gas flows into the inlet and to assume an actuated position when gas does flow into the inlet,
    (g) means for detecting the position of the flow responsive member, and
    (h) means connected to said flexible diaphragm for damping vibrations in said flexible diaphragm.

5. The switch of claim 4 in which the damping means comprises a damping member which vibrates at a frequency which destructively interferes with the vibrations of said flexible diaphragm.

6. The switch of claim 4 in which the flexible diaphragm comprises a first elastomeric disc and in which the damping member comprises a second elastomeric disc.

7. The switch of claim 6 in which the diameter of the second disc is smaller than the diameter of the first disc.

8. The switch of claim 6 in which the center of said first disc is connected to the center of said second disc.

* * * * *